United States Patent
Nycz

(10) Patent No.: US 8,838,249 B2
(45) Date of Patent: Sep. 16, 2014

(54) IMPLANTABLE TISSUE GROWTH STIMULATOR

(75) Inventor: Jeffrey H. Nycz, Warsaw, IN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 13/293,759

(22) Filed: Nov. 10, 2011

(65) Prior Publication Data

US 2012/0059434 A1    Mar. 8, 2012

Related U.S. Application Data

(63) Continuation of application No. 11/344,668, filed on Feb. 1, 2006, now Pat. No. 8,078,282.

(51) Int. Cl.
*A61N 1/00* (2006.01)
*A61N 1/20* (2006.01)
*A61N 1/32* (2006.01)

(52) U.S. Cl.
CPC ............ *A61N 1/205* (2013.01); *A61N 1/326* (2013.01)
USPC .......................................................... 607/51

(58) Field of Classification Search
CPC ......... A61N 1/326; A61N 1/205; A61N 1/40; A61F 2/32; A61F 2/34; A61F 2/38; A61F 2/36
USPC .................... 607/50–51, 52; 623/13.11–23.76
See application file for complete search history.

(56) References Cited

U.S. PATENT DOCUMENTS

| | | |
|---|---|---|
| 3,181,528 A | 5/1965 | Brackin |
| 3,783,880 A | 1/1974 | Kraus |
| 4,026,304 A | 5/1977 | Levy |
| 4,195,367 A | 4/1980 | Kraus |
| 4,195,643 A | 4/1980 | Pratt, Jr. |
| 4,430,999 A | 2/1984 | Brighton et al. |
| 4,506,673 A | 3/1985 | Bonnell |

(Continued)

FOREIGN PATENT DOCUMENTS

| | | |
|---|---|---|
| DE | 10342823 A1 | 9/2003 |
| EP | 344770 A1 | 12/1989 |

(Continued)

OTHER PUBLICATIONS

European Patent Patent Office, International Searching Authority, Notification of Transmittal of the International Search Report and Written Opinion of the International Searching Authority or the Declaration, International Application No. PCT/US2007/061425, May 7, 2007, 13 pages.

(Continued)

*Primary Examiner* — Christopher D Koharski
*Assistant Examiner* — Roland Dinga
(74) *Attorney, Agent, or Firm* — Sorell, Lenna & Schmidt LLP

(57) ABSTRACT

An implantable tissue growth stimulator is disclosed. The implantable tissue growth stimulator includes electronic circuitry to alter the voltage output by the stimulator. The implantable tissue growth stimulator may he controlled from an external device via wireless communication. The implantable tissue growth stimulator may be configured for use with an implants in particular, the implantable tissue growth stimulator may be incorporated into an orthopedic device such as a hip prosthesis. The implantable tissue growth stimulator may be used to stimulate bone growth.

35 Claims, 3 Drawing Sheets

(56) References Cited

U.S. PATENT DOCUMENTS

| | | | |
|---|---|---|---|
| 4,519,394 A | | 5/1985 | Black et al. |
| 4,672,963 A | | 6/1987 | Barken |
| 5,030,236 A | | 7/1991 | Dean |
| 5,178,148 A | | 1/1993 | Lacoste et al. |
| 5,394,875 A | | 3/1995 | Lewis et al. |
| 5,413,116 A | * | 5/1995 | Radke et al. .............. 600/590 |
| 5,441,527 A | * | 8/1995 | Erickson et al. ............ 607/51 |
| 5,480,420 A | | 1/1996 | Hoegnelid et al. |
| 5,533,519 A | | 7/1996 | Radke et al. |
| 5,565,005 A | | 10/1996 | Erickson et al. |
| 5,855,592 A | * | 1/1999 | McGee et al. ................ 607/4 |
| 5,976,148 A | | 11/1999 | Charpenet et al. |
| 6,120,502 A | | 9/2000 | Michelson |
| 6,245,109 B1 | | 6/2001 | Mendes et al. |
| 6,445,955 B1 | | 9/2002 | Michelson et al. |
| 6,447,448 B1 | | 9/2002 | Ishikawa et al. |
| 6,585,647 B1 | | 7/2003 | Winder |
| 6,605,089 B1 | | 8/2003 | Michelson |
| 6,656,135 B2 | | 12/2003 | Zogbi et al. |
| 6,733,458 B1 | | 5/2004 | Steins et al. |
| 6,849,463 B2 | | 2/2005 | Santini, Jr. et al. |
| 6,955,642 B1 | | 10/2005 | Simon |
| 7,431,734 B2 | | 10/2008 | Danoff et al. |
| 2001/0049527 A1 | | 12/2001 | Cragg |
| 2002/0107649 A1 | | 8/2002 | Takiguchi et al. |
| 2003/0199783 A1 | | 10/2003 | Bloom et al. |
| 2004/0143302 A1 | | 7/2004 | Sieracki et al. |
| 2004/0236192 A1 | | 11/2004 | Necola et al. |
| 2005/0010300 A1 | | 1/2005 | Disilvestro et al. |
| 2005/0119587 A1 | | 6/2005 | Roessler et al. |
| 2005/0177203 A1 | | 8/2005 | Brighton et al. |
| 2006/0009856 A1 | | 1/2006 | Sherman et al. |

FOREIGN PATENT DOCUMENTS

| | | |
|---|---|---|
| EP | 1238630 A2 | 9/2002 |
| EP | 1442715 A2 | 1/2004 |
| WO | 9217113 A1 | 10/1992 |
| WO | 9733513 A1 | 9/1997 |
| WO | 0230338 A1 | 4/2002 |
| WO | 2005007025 A2 | 1/2005 |
| WO | 2005120203 A2 | 12/2005 |
| WO | 2006105098 A2 | 10/2006 |

OTHER PUBLICATIONS

European Patent Patent Office, International Searching Authority, Notification of Transmittal of the International Search Report and Written Opinion of the International Searching Authority or the Declaration, International Application No. PCT/US2007/061388, May 25, 2007, 13 pages.

European Patent Patent Office, International Searching Authority, Notification of Transmittal of the International Search Report and Written Opinion of the International Searching Authority or the Declaration, International Application No. PCT/US2007/061446, Jul. 4, 2007, 12 pages.

European Patent Patent Office, International Searching Authority, Notification of Transmittal of the International Search Report and Written Opinion of the International Searching Authority or the Declaration, International Application No. PCT/US2007/062312, Jul. 5, 2007, 13 pages.

Orme, et al. "Engineered Titanium for Improved Biological Response", Lawrence Livermore National Laboratory, US Department of Energy (Jan. 23, 2002).

http:/www.ebimedical.com/products/detail.cfm?p=0D, pp. 1-3, retrieved Dec. 14, 2005.

http:/www.ebimedical.com/products/detail.cfm?p=0F, retrieved Dec. 14, 2005.

http:/www.ebimedical.com/products/detail.cfm?p=00, pp. 1 and 2, retrieved Dec. 14, 2005.

http:/www.ebimedical.com/products/detail.cfm?p=OE, pp. 1 and 2, retrieved Dec. 14, 2005.

http:/www.orthofix.com, pp. 1-4.

http:/www.ebimedical.com/products/detail.cfm?p=0C, pp. 1-3, retrieved Dec. 14, 2005.

* cited by examiner

US 8,838,249 B2

IMPLANTABLE TISSUE GROWTH STIMULATOR

CROSS-REFERENCE TO RELATED APPLICATION

This application is a continuation application of U.S. application Ser. No. 11/344,668, filed on Feb. 1, 2006, now U.S. Pat. No. 8,078,282, which is hereby incorporated by reference in its entirety.

FIELD OF THE INVENTION

The present invention, is directed to improved instrumentation and methods for stimulating tissue growth. More particularly, in one aspect the present invention is directed to instruments and methods for stimulating tissue growth near an implant.

BACKGROUND OF THE INVENTION

The present invention relates to promoting and stimulating tissue growth. The invention may have particularly useful application in the stimulation of bone growth as it relates to artificial implants and, in particular, total joint replacement surgeries including the implantation of hip, knee, spine, shoulder, ankle, and wrist prostheses. The invention may be utilized to help facilitate incorporation of the implant into the body.

Within the field of surgery, bone growth stimulators are often used to promote bone growth by subjecting the bone to an electric field to create a negative charge in the area where bone growth is sought. It has been shown that changing the strength of the electric field and resulting negative charge over time can further stimulate bone growth. Bone growth stimulators are often used in the treatment of nonunions and bone graft surgeries. However, bone growth is very important to the incorporation of various types of implants as well. For example, in a successful total hip replacement surgery the acetabular cup of the implant is fused with the bone of the acetabulum. Often only 20-40 percent of the connection between the acetabular cup and the acetabulum is fused bone; the rest, 60-80 percent, is a fibrous membrane. Increasing the amount of bone fusion between the implant and the bone leads to better incorporation of the implant and decreases chances of implant loosing and the potential need for revision surgery.

Therefore, there remains a need for improved instruments and methods of promoting tissue growth as related to artificial implants and, in particular, total joint implants.

SUMMARY OF THE INVENTION

The present invention provides a bone growth stimulator for use with an orthopaedic device. The bone growth stimulator includes a plurality of electrical conductors arranged in a preformed geometry and adapted to provide electrical stimulation to a bone. The bone growth stimulator also includes a sheath having a first surface for engaging the orthopaedic device and a second surface for engaging the bone. The sheath is adapted for at least partially maintaining the geometry of the plurality of electrical conductors.

In another aspect, the present invention provides a method of providing bone growth stimulation within a body. The method includes providing a bone growth stimulator—the bone growth stimulator including a plurality of electrical conductors adapted to provide electrical stimulation to a bone and a sheath. The sheath has a first surface for engaging an orthopaedic device and a second surface for engaging the bone. The sheath is also adapted for at least partially maintaining the position of the plurality of electrical conductors. The method also includes inserting the bone growth stimulator into the body adjacent a bone and operating the bone growth stimulator to provide electrical stimulation to the bone.

In another aspect, the present invention provides a bone growth stimulator for use within a body. The bone growth stimulator includes a plurality of electrical conductors adapted to provide electrical stimulation to a bone and a malleable sheath having a first surface for engaging a tissue of the body. The malleable sheath is adapted for at least partially maintaining the position of the plurality of electrical conductors.

Further aspects, forms, embodiments, objects, features, benefits, and advantages of the present invention shall become apparent from the detailed drawings and descriptions provided herein.

DESCRIPTION OF THE PREFERRED EMBODIMENTS

Figure 1:
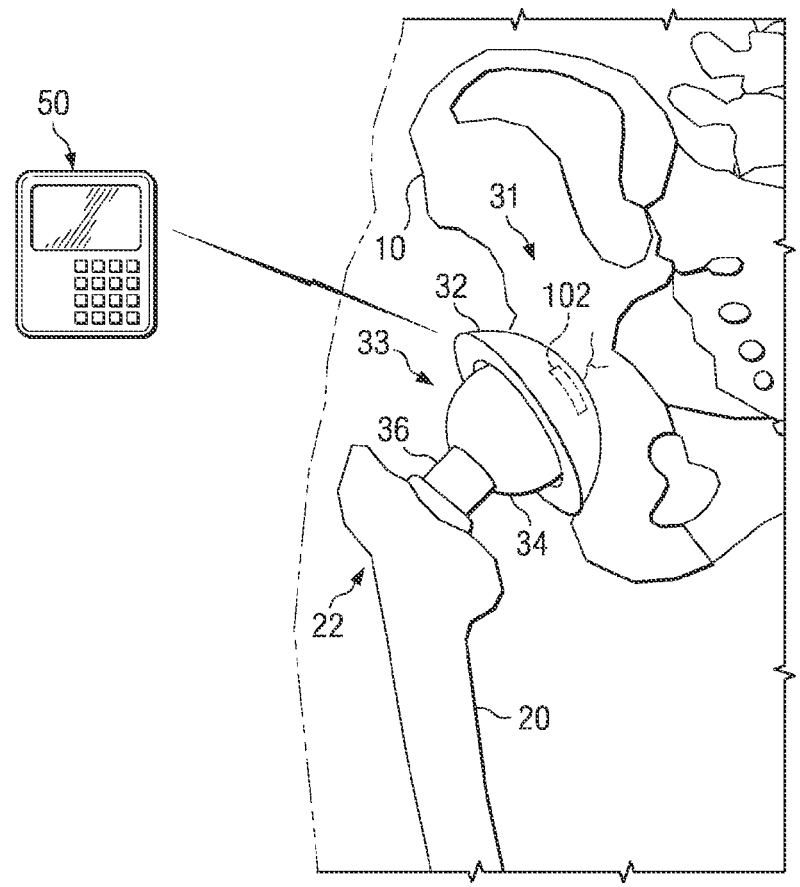
FIG. 1 is a front view of an implantable bone growth stimulation system of a hip prostheses in wireless communication with an external device according to one embodiment of the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended. Any alterations and further modifications in the described devices, instruments, methods, and any further application of the principles of the invention as described herein are contemplated as would normally occur to one skilled in the art to which the invention relates.

Figure 2A:
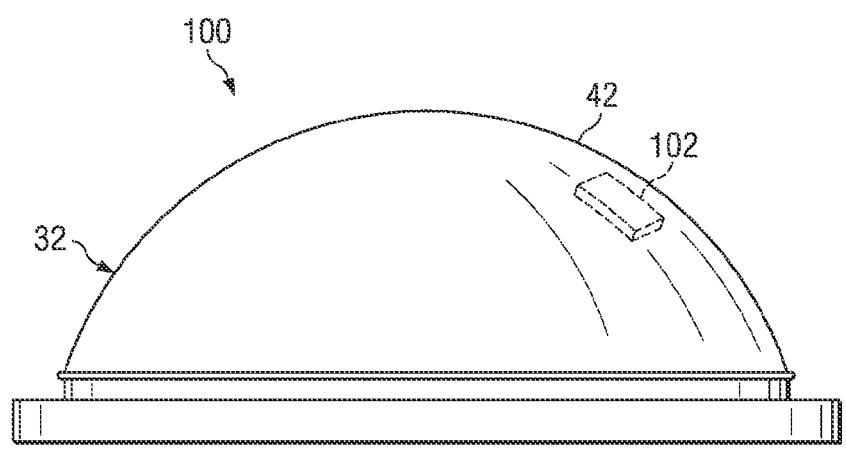
FIG. 2A is an enlarged front view of the implantable bone growth stimulation system of FIG. 1.
Figure 2B:
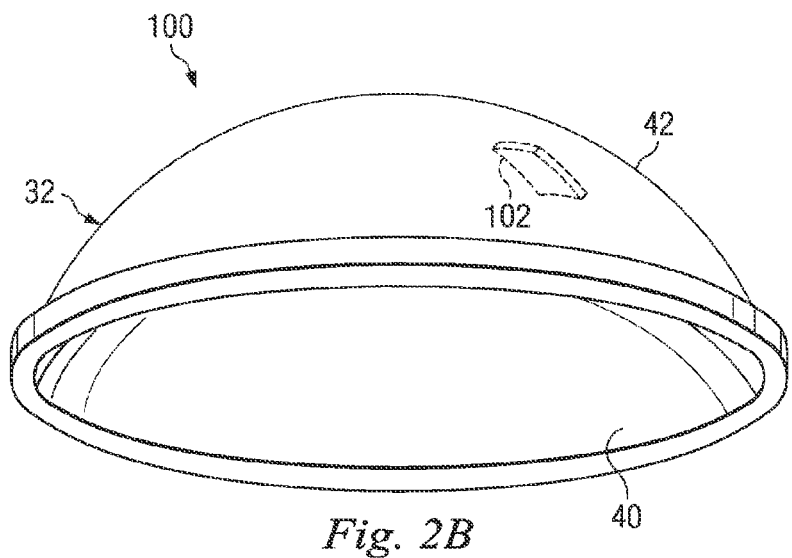
FIG. 2B is a perspective view of the implantable bone growth stimulation system of FIG. 1.
Figure 3:
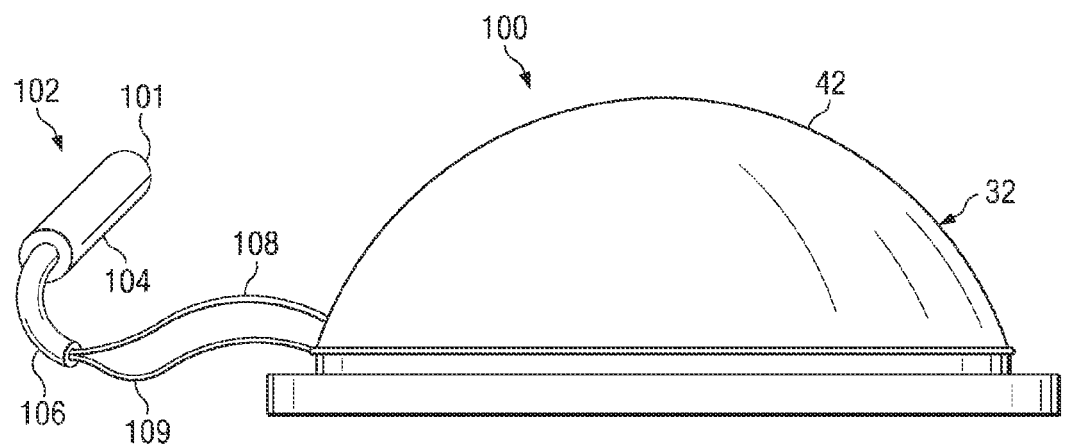
FIG. 3 is an enlarged front view of an implantable bone growth stimulation system according to one embodiment of the present invention.

Referring now to FIGS. 1-3, shown therein is an implantable bone growth stimulation system 100 according to one embodiment of the present invention. The bone growth stimulation system 100 is shown with respect to a total hip prosthesis 30. The hip prosthesis 30 includes an acetabular component 31 and a femoral component 33. The acetabular component 31 comprises an acetabular cup 32 having an exterior or bone engaging surface 42 configured for engagement with a prepared portion of the patient's acetabulum 10. The femoral component 33 comprises a femoral head 34 and a femoral stem 36. The femoral head 34 is configured for movable engagement with an internal surface 40 of the acetabular cup 32 so as to create ball-in-socket motion. The stem 36 of the femoral component is adapted for engaging a proximal portion 22 of the patient's femur 20. The ball-in-socket motion between the femoral head 34 and the acetabular cup 32 simulates the motion of the patient's natural hip joint.

It is contemplated that the hip prosthesis 30 may be made out of titanium or titanium alloys. Studies have shown that increasing the voltage across titanium will produce an increasing thickness of the oxide layer. Consequently, reducing the voltage across the titanium hip prosthesis 30 alters the oxide layer in a way that causes a biological response that promotes bone growth. Titanium is not the only available material. It is fully contemplated that the hip prosthesis 30 may be out of any suitable material for a hip prosthesis such as, for example and without limitation, any suitable biocompatible material including metals such as cobalt-chromium alloys, titanium alloys, nickel titanium alloys, and/or stainless steel alloys, Ceramic materials such as aluminum oxide or alumina, zirconium oxide or zirconia, compact of particulate diamond, arid/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. Also the hip prosthesis may be formed from a plurality of materials thus permitting metal on metal, metal on ceramic, metal on polymer, ceramic on ceramic, ceramic on polymer, or polymer on polymer constructions. In this regard, it is fully contemplated that the hip prosthesis 30 may be made up of a plurality of materials to achieve the desired bone stimulation effects. For example, the hip prosthesis may be made substantially out of a polymer or ceramic but include an outer coating or layer of titanium. It is further contemplated that the hip prosthesis 30 may include insulating layers or portions to limit or define the areas where current flows and therefore the areas of bone growth stimulation.

The implantable bone growth stimulation system 100 includes electronics 102. As shown in FIGS. 1-2B, it is contemplated that the electronics 102 may be disposed within a portion of the hip prosthesis 30. It is also contemplated, however, that the electronics 102 may be disposed outside of the hip prosthesis 30. For example, but without limitation, the electronics 102 may be detachably engaged with the hip prosthesis, permanently attached to the hip prosthesis, placed in natural tissue adjacent the hip prosthesis, or placed in natural tissue distal to the hip prosthesis. In this regard, as shown in FIG. 3 it is contemplated that the electronics 102 may be located within a housing 201 having an outer surface 204 adapted for anchoring the electronics in a position with respect to the surrounding tissue. The outer surface 204 of the housing 201 may be shaped, include tissue anchoring surfaces, or otherwise configured for maintaining the relative position of the implant with respect to the surrounding tissue. For example, but without limitation, the outer surface 204 may be threaded, knurled, ribbed, roughened, etched, sintered, have a bone ingrowth surface, or include protrusions to engage the surrounding tissue or the hip prosthesis. Additionally, separately, or, in combination with the foregoing, the outer surface 204 may be at least partially coated with chemical or biologic agents for promoting adhesion to the surrounding tissue and/or growth of the tissue onto the outer surface of the housing.

The electronics 102 may include such things as integrated circuits, power supplies, communication devices/telemetry circuitry, memory, signal processors, electrical outputs, transformers, resistors, electrical leads, electrodes, timers, coils, sensors, capacitors, or other electronic components useful for implantable bone growth stimulation. In the current embodiment, the electronics 102 are adapted for producing a voltage across the titanium acetabular cup 32. It is contemplated that the voltage may be created by causing an electrical current to pass through the acetabular cup 32. The electrical stimulation created by the voltage may be utilized to accelerate bone growth around the acetabular cup 32. As described above, increasing the voltage across titanium produces an increasing thickness of the oxide layer. However, reducing the voltage across the titanium hip prosthesis 30 alters the oxide layer in a way that causes a biological response that promotes bone growth. In this respect, it is contemplated that the voltage may be varied to further encourage bone growth. Thus, changing the voltage across the acetabular cup 32 may be used to encourage fusion of the acetabulum 10 to the exterior. surface 42 the acetabular cup, which can lead to better incorporation of the hip prosthesis 30, better implant functionality, a decreased chance of implant loosing, and a decreased likelihood of revision surgery.

It is further contemplated that the outer surface 42 of the acetabular cup 32 may be treated to encourage bone growth by means other than providing electrical stimulation. The outer surface 42 may include features or coatings that enhance the fixation of the implanted hip prosthesis 30. For example, the outer surface 42 may be roughened such as by chemical etching, bead-blasting, sanding, grinding, sintering, mesh, beads, serrating, and/or diamond-cutting. All or a portion of the outer surface 42 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

As shown in FIG. 1, the electronics 102 are configured for communication with an external device 50. In particular, the electronics 102 may be configured for communication via wireless telemetry with the external device 50. For example, but without limitation, it is contemplated that the external device 50 and electronics 102 may communicate via RFID, inductive telemetry, acoustic energy, near infrared energy, "Bluetooth," and computer networks are all possible means of wireless communication. It is also contemplated that the external device 50 and the electronics 102 may communicate via wired communication means as well. In this manner, the external device 50 may be utilized to control the amount and degree of bone growth stimulation being provided by the system 100. For example, it is contemplated that the implantable bone growth stimulation system 100 may not be powered. Thus, external device 50 may be used to provide selective power to the system 100 for stimulating bone growth. In this sense, communication between the electronics 102 and the external device 50 are intended to include power transfers as well as information or data transfers. Further, the external device 50 may control the amount of power the system 100 receives and thereby determine the amount of voltage the system puts out. On the other hand, the external device 50 may provide the system 100 with sufficient power to produce voltage outputs in the full range of the system, between 0.5 V and 10 V, and provide a signal indicating the desired voltage level to be produced. In this way, the external device 50 may be used to alter the voltage of the system 100 over time.

On the other hand, it is also contemplated that the implantable bone growth stimulation system 100 may be powered.

For example, the electronics 102 may include a battery. Battery is intended to mean any device capable of storing and providing power to the system 100. The battery may be a lithium iodine battery similar to those used for other medical implant devices such as pacemakers. However, the battery may be any type of battery suitable for implantation. Further, it is fully contemplated that the battery may be rechargeable. It is also contemplated that the battery may be configured so that it can be recharged by an external device so as to avoid the necessity of a surgical procedure to recharge or replace the battery. In one embodiment the battery is rechargeable via inductive coupling.

In the case of the system 100 being powered, it is contemplated that the external device 50 may be utilized to control various aspects of the stimulation system. For example, when the system 100 is powered it may be configured to provide constant bone growth stimulation or to provide stimulation at specific intervals. The stimulation can be provided without the presence of the external device 50. However, the external device 50 may be used to change parameters of the system such as whether stimulation is constant, the interval of stimulation, and the voltage of the system. The parameters may be changed in light of the patient's condition and the treating physician's preferences. In particular, it is contemplated that the voltage of the system 100 may be altered over time by the external device 50 to encourage bone growth.

On the other hand, it is also contemplated that when the system 100 is powered the electronics 102 may be programmed to provide stimulation according to a predetermined routine. Thus, the system 100 may progress through a series of various intervals and voltages without need for communication with the external device. Further, it is contemplated that the implantable bone growth stimulation system 100 may determine the appropriate stimulation doses and strengths by itself. As more fully described in a commonly assigned patent application entitled "Implantable Sensor," an implantable sensor may be utilized to determine bone density and changes in bone density. The patent application entitled "Implantable Sensor," Ser. No. 11/344,667 is incorporated herein by reference in its entirety. The implantable bone growth stimulation system 100 may include a sensor similar to those described in the above referenced patent application. Based upon the bone density data received from the sensor, the system 100 may tailor the treatment patterns to further encourage bone growth. It is contemplated that the system 100 may utilize signal processing and stored algorithms for determining the appropriate stimulation patterns.

Referring now to FIG. 3, shown therein is the implantable bone growth stimulation system 100 adapted for placement in natural tissue. As described above, the electronics 102 are located within a housing 101 having an outer surface 104 adapted for anchoring the electronics in a position with respect to the surrounding tissue. It is fully contemplated that the housing 101 may be shaped to facilitate implantation via a catheter. Without limitation, it is contemplated that the housing may take the shape of an elongated cylinder, as shown in FIG. 3, to allow placement via a catheter. In one aspect, the diameter of the housing 101 is smaller than 10 mm. In another aspect, the diameter may be 4 mm or smaller. Though the implantable bone growth stimulation system 100 may be implanted during the same surgery as the implantation of the hip prosthesis 30, it is also fully contemplated that the implantable bone growth stimulation system 100 may be inserted after implanting the hip prosthesis. For this reason, the system 100 may be adapted for implantation via a minimally invasive technique.

The implantable bone growth stimulation system 100 includes leads 108, 109 that connect the electronics 102 to the outer surface 42 of the acetabular cup 32. It is contemplated that lead 108 be an anode lead and lead 109 be a cathode lead, or vice-versa, to provide electrical current and, therefore, a voltage to the bone engaging outer surface 42 of the actabular cup 32. In particular, the leads 108, 109 are adapted for supplying the voltages and change in voltages from the electronics 102 to the acetabular cup 32. Though the leads 108, 109 are shown as attaching to the outer surface 42 of the acetabular cup 32, it is fully contemplated that the leads may connect anywhere on the acetabular cup 32. Further, it is contemplated that the acetabular cup 32 may include connection points or interfaces (not shown) designed specifically to receive the leads 108, 109. The connection points may be located to facilitate transfer of the voltages from the electronics 102 to the desired areas for bone growth stimulation. As shown in FIG. 3, it is contemplated that the leads may be encased in a tubing 106. The tubing 106 may be used to protect the leads. It is fully contemplated that the bone growth stimulation 100 not include tubing 106. It is also fully contemplated that the leads 108, 109 may be incorporated into a single lead or wire.

It is fully contemplated that the leads 108, 109 may be implanted prior to the housing 101 holding the electronics 102. In this regard, the leads 108, 109 may be attached to the acetabular cup 32 using a minimally invasive technique as it will only be necessary to place the very small leads, having a diameter under 2 mm, in contact with the acetabular cup. In other embodiments the leads have a diameter less than 1 mm. The leads 108, 109 may then be attached to the electronics 102 at a point outside of the joint at a point where the housing 101 is implanted via a catheter. Placement of the housing 101 closer to the skin surface may facilitate better wireless communication with the external device 50 and allow for easier implantation. It is fully contemplated that the leads 108, 109 may attached or connected to the acetabular cup 32 at the time of the total hip replacement surgery and then the housing and electronics connected to the leads at a later time to complete the bone growth stimulation system 100.

Figure 4:
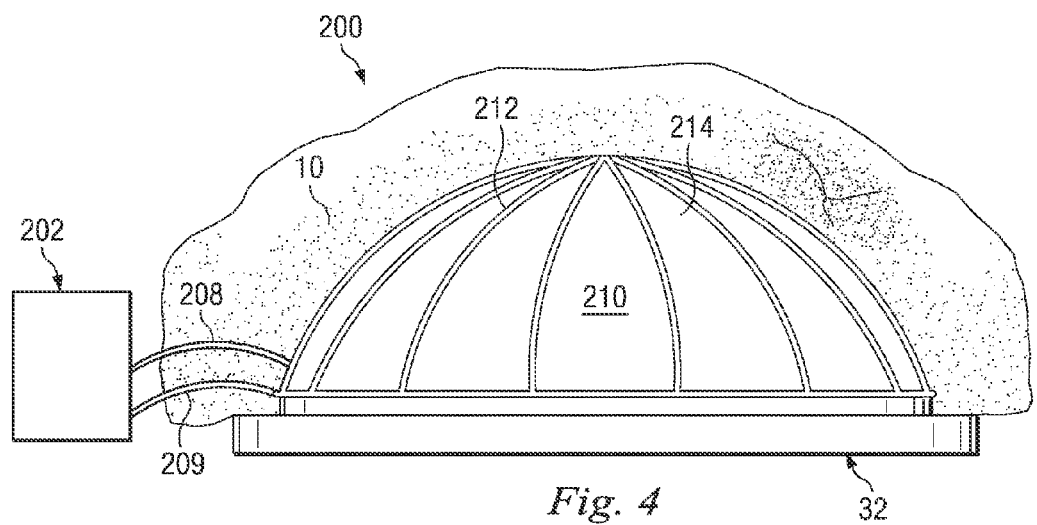
FIG. 4 is an enlarged front view of a bone growth stimulator positioned on an acetabular cup and engaged with an acetabulum according to one embodiment of the present invention.
Figure 5:
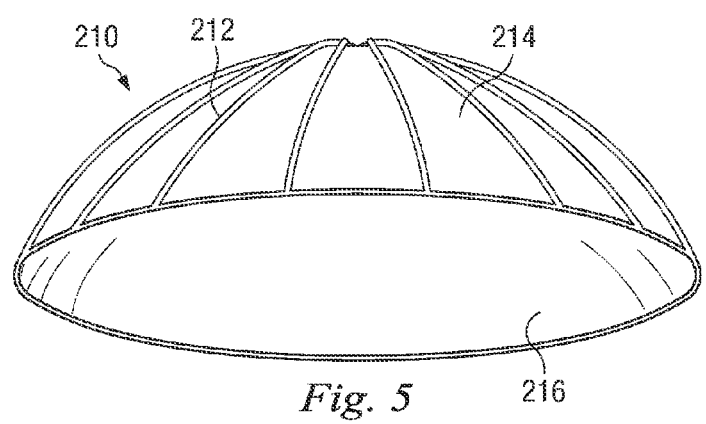
FIG. 5 is an enlarged prospective view of the bone growth stimulator of FIG. 4.

Referring now to FIGS. 4-5, shown therein is an implantable bone growth stimulator 200 according to one embodiment of the present invention. The implantable bone growth stimulator 200 may be substantially similar to the bone growth stimulation system 100 described above except for the differences noted below. Bone growth stimulator 200 includes electronics 202, leads 208 and 209, a thin film or sheath 210, a plurality of electrical conductors 212, and an insulating layer 214. While electronics 202 are shown separate and apart from the sheath 210 it is fully contemplated that the electronics may be incorporated into the sheath itself. It is also contemplated that the electronics 202 may be carried by a resorbable membrane, such as PLA or PLDLA. On the other hand, it is also fully contemplated that the electronics 202 may be incorporated into a housing similar to housing 101 described above with respect to bone growth stimulation system 100.

The sheath 210 is adapted for lining the portion of the acetabulum 10 prepared to receive the acetabular cup 32. The sheath 210 includes inner surface 216 adapted for engaging the outer surface 42 of the acetabular cup 32. In that regard, it is fully contemplated that the inner surface 216 may include features or treatments to help facilitate engagement with the acetabular cup 32. For example, the inner surface 216 of the sheath 210 may include projections or recesses to mate with recesses or projections of the outer surface 42. The inner surface may also be roughened, knurled, threaded, ribbed, etched, sintered, or shaped or treated in any other manner to encourage engagement. It is contemplated that the sheath 210 may be inserted so as to line the acetabulum 10 prior to the implantation of the acetabular cup 32 so that when the acetabular cup is implanted it will seal the sheath into place. It is also contemplated, however, that the sheath 210 may be adapted to engage the acetabular cup 32 prior to implantation so that when the acetabular cup 32 is implanted the sheath 210 will then line the acetabulum 10 in a position to stimulate bone growth.

It is contemplated that the sheath 210 may be malleable so as to conform to the interface between the acetabulum 10 and the acetabular cup 32. Where the sheath 210 is adapted to be malleable it is contemplated that it will be made of materials such as PLDLA and collagen. Having a malleable material allows the bone growth stimulator 200 to be utilized with a wide variety of sizes and types of acetabular cups produced by a variety of manufacturers. It is also contemplated that the sheath 210 may be formed of a more rigid material designed to precisely fit over the acetabular cup 32. In this approach the sheath 210 must be formed so that inner surface 216 mates with outer surface 42 of the acetabular cup 32 to ensure a secure fit. Materials appropriate for a more rigid sheath 210 include certain polymers, including PLDLA, and reinforced collagen sheets. Whether the sheath 210 is malleable or more rigid, it is fully contemplated that the sheath may be made of a resorbable material.

In one aspect, the grid of electrical conductors 212 may be placed over an implant, such as an acetabular cup 32. This can occur in a production facility or in the operating room. Under one approach, a material such as PEG-DA, which forms a hydrogel type material, may be combined with an osteoconductive or osteoinductive material. The combination may then be applied to the surface of the implant. The hydrogel material may be cured by exposure to ultraviolet light, which bonds the PEG-DA mixture to the substrate of the implant. Further, the cured combination of PEG-DA and osteoconductive or osteoinductive material may be resorbable when exposed to fluids in the body.

The bone growth stimulator 200 includes a plurality of electrical conductors 212. The plurality of electrical conductors 212 is adapted for producing voltage or electric current to stimulate bone growth. Electrical conductors in this sense are meant to signify all types of components, including wires, that may be utilized to carry a current or create a potential difference or voltage to stimulate bone growth. The plurality of electrical conductors 212 is further adapted to produce various voltages over a range from 0.5 V to 10 V. In this regard, it is contemplated that each of the electrical conductors comprising the plurality of electrical conductors may be configured to produce all of the voltages within this range, a plurality of voltages within the range, or a single voltage within the range. In this regard, it is contemplated that the bone growth stimulator 200 may provide different voltages by varying the specific electrical conductors activated when providing stimulation, varying the voltages output by each wire, or a combination of both.

Though the electrical conductors 212 are shown as extending from a center point at the top of the acetabular cup 32, it is fully contemplated that the plurality of electrical conductors may be configured in any other way to stimulate bone growth. It is also contemplated that the electrical conductors may be preformed in a geometry designed to encourage bone growth. However, it is also fully contemplated that each physician may select the pattern for the electrical conductors based on factors such as the location of the bone growth stimulator, the type of implant, the age and activity of the patient, the type of tissue or bone being stimulated, or any other relevant factors. For this reason, it is fully contemplated that the electrical conductors 212 may be malleable as well to allow the doctor to shape the electrical conductors to the appropriate shape and geometry. The electrical conductors 212 may be arranged into a flat pattern. For example, but without limitation, the electrical conductors 212 may be arranged concentrically, in a zig-zag pattern, in a criss-cross pattern, as a grid, as a spiral, or any other flat configuration. It is not necessary for the pattern to be symmetrical, though it may be. It is also fully contemplated that the flat patterns may be flexible or malleable so that when placed onto an orthopaedic device the pattern can conform to the contours of the device surface.

The electrical conductors 212 may also be arranged in 3-dimensional geometries. In this respect, it is contemplated that the electrical conductors would be shaped to substantially match a prepared surface of a bone, the surface on an orthopaedic device, or both. Thus, the geometry of the electrical conductors may be of any shape to facilitate engagement with a bone or orthopaedic device. The sheath 210 is adapted to at least partially maintain the pattern, shape, and/or geometry of the electrical conductors 212. In this respect, it is fully contemplated that the sheath 210 and the electrical conductors 212 may be malleable so as to allow some movement and changing of the pattern, shape, or geometry to allow a secure fit between the bone, the bone growth stimulator, and the implant.

It is also contemplated that the sheath 210 may consist of multiple layers of material. The various layers may be made out of similar or different materials. In this respect, the electrical conductors 212 may be positioned between layers of the sheath 210 so that the electrical conductors are encased or bonded between the layers. Positioning the electrical conductors 212 between layers of the sheath 210 can help maintain the arrangement of the conductors as well as provide protection to the conductors. It is fully contemplated that different electrical conductors within the plurality of electrical conductors 212 may be disposed between different layers of the sheath. That is, several electrical conductors may be disposed between layers A and B (not shown) of the sheath, others between layers B and C (not shown), and so on. There may be layers with no electrical conductors between them. It is also fully contemplated that the electrical conductors may be disposed on an outside surface of the sheath 210. The outer surface of the sheath 210 may include recesses, grooves, connectors, or other features adapted for maintaining the electrical conductors 212 on the outer surface. Though it has been described as a plurality of electrical conductors 212, it is fully contemplated that a single, connected conductor or wire may be utilized instead. Further, the plurality of electrical conductors may be connected to each other or may remain separate.

The electronics 202 are shown as being apart from the sheath 210 and electrical conductors 212. As mentioned above, however, it is fully contemplated that the electronics may be incorporated into the sheath 210 or otherwise attached to the sheath. It is also contemplated that the electronics be disposed with a portion of the hip prosthesis 30. Regardless of where the electronics 202 are disposed, the electronics are in communication with or connect to the plurality of electrical conductors 212. As shown in FIG. 4, where the electronics 202 are disposed apart from the sheath 210 leads 208, 209 may be utilized to connect the electronics to the plurality of electrical conductors 212. In this way, the leads 208, 209 may be utilized to carry the voltage signals from the electronics 202 to the plurality of electrical conductors 212, where the electrical conductors can output the appropriate voltages to encourage bone growth. Again it is contemplated that the voltages will be varied over time to stimulate additional bone growth and changes in voltages may be preprogrammed into the stimulator 200 or implemented and changed by the external device 50.

Finally, the bone growth stimulator 200 may include an insulation layer 214. It is fully contemplated that the sheath 110 may be made of an insulating material so that the sheath acts as the insulating layer. The insulation layer 214 may be used to shield the acetabular cup 32 from the voltages output by the plurality of electrical conductors 212. The insulation layer 214 may also be utilized to control the regions of bone growth stimulation. For example, in areas where bone growth is not desired an insulation layer may be utilized to shield the area from the stimulation provided by the bone growth stimulator 200. However, it is not necessary for the bone growth stimulator 200 to include an insulation layer 214. The bone growth stimulator 200 may be utilized without an insulation layer and still be effective to stimulate bone growth. For example, the plurality of electrical conductors 212 may be attached directly to the outer surface 42 of the acetabular cup 32 so as to create a voltage across the acetabular cup itself as well as the electrical conductors. In this regard, the bone growth stimulator 200 may utilize the method of stimulation using acetabular cup as described in relation with bone growth stimulation system 100 as well as providing direct bone growth stimulation through the electrical conductors 212.

While the foregoing description has been with particular emphasis on the acetabular cup of a hip prosthesis, it is fully contemplated that the disclosed bone growth stimulators may have further applications throughout the body. For example, it is fully contemplated that bone growth stimulators according to the present invention may be utilized with any implant that engages bone including, but not limited to ankle, knee, hip, spine, elbow, wrist, finger, and jaw implants, intramedullary nails, screws, rods, plates, and other trauma applications. It is also fully contemplated that the shape and size of the bone growth stimulators may be adapted for the various types of implants. Similarly, while the description has been made with particular emphasis on bone growth, the present invention may utilized to encourage other tissue growth. For example, the invention may have application in the repair, of ligaments, such as needed with ACL reconstruction.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A bone growth stimulator for use with an orthopaedic device including an acetabular cup with a hemispherical exterior surface, the bone growth simulator comprising:
   a plurality of electrical conductors arranged in a preformed geometry and adapted to provide electrical stimulation to a bone; and
   a sheath comprising a hemispherical configuration and having a first surface for engaging the exterior surface and a second surface for engaging the bone, the sheath adapted for at least partially maintaining the geometry of the plurality of electrical conductors, the plurality of electrical connectors each extending radially from a common point.

2. The bone growth stimulator of claim 1, wherein the sheath is malleable.

3. The bone growth stimulator of claim 2, wherein the plurality of electrical conductors is malleable.

4. The bone growth stimulator of claim 1, wherein the sheath is made substantially of an insulating material.

5. The bone growth stimulator of claim 4, wherein the sheath is adapted to shield the orthopaedic device from the electrical stimulation of the bone.

6. The bone growth stimulator of claim 1, wherein the plurality of electrical conductors are adapted for providing electrical stimulation over a range of voltages between 0.5 V to 10 V.

7. The bone growth stimulator of claim 6, wherein the plurality of electrical conductors are adapted for providing electrical stimulation over a range of voltages between 2 V to 6 V.

8. The bone growth stimulator of claim 6, wherein each of the electrical conductors of the plurality of electrical conductors is adapted to provide electrical stimulation for at least one voltage level in the range of voltages.

9. The bone growth stimulator of claim 8, wherein each of the electrical conductors of the plurality of electrical conductors is adapted to provide electrical stimulation at a voltage different from at least one other electrical conductor.

10. The bone growth stimulator of claim 8, wherein each of the electrical conductors of the plurality of electrical conductors is adapted to provide electrical stimulation at a plurality of voltages in the range of voltages.

11. The bone growth stimulator of claim 10, wherein each of the electrical conductors of the plurality of electrical conductors is adapted to provide electrical stimulation over the entire range of voltages.

12. The bone growth stimulator of claim 1, further comprising an internal controller adapted for controlling a parameter of the electrical stimulation provided by the plurality of electrical conductors.

13. The bone growth stimulator of claim 12, wherein the internal controller is adapted for communication with an external device.

14. The bone growth stimulator of claim 13, wherein the external device is adapted for determining a parameter controlled by the internal controller.

15. The bone growth stimulator of claim 13, wherein the internal controller and plurality of electrical conductors are adapted to receive power from the external device.

16. The bone growth stimulator of claim 15, wherein the plurality of electrical conductors are adapted to provide electrical stimulation only when the external device provides power to the plurality of electrical conductors.

17. The bone growth stimulator of claim 12, wherein the internal controller is adapted to control a plurality of parameters of the electrical stimulation.

18. The bone growth stimulator of claim 17, wherein at least one parameter is voltage.

19. The bone growth stimulator of claim 1, wherein the preformed geometry is substantially flat.

20. The bone growth stimulator of claim 1, wherein the plurality of electrical conductors is adapted for at least partially maintaining the preformed geometry.

21. The bone growth stimulator of claim 20, wherein the plurality of conductors are reinforced.

22. The bone growth stimulator of claim 1, wherein the orthopaedic device is a hip prosthesis.

23. The bone growth stimulator of claim 1, wherein the sheath comprises multiple layers, at least one of the electrical conductors being disposed between two layers of the sheath.

24. The bone growth stimulator of claim 1, wherein the sheath comprises collagen.

25. The bone growth stimulator of claim 1, wherein the sheath is provided without an insulation layer.

26. A bone growth stimulator for use within a body, comprising:
   a plurality of electrical conductors adapted to provide electrical stimulation to a bone; and
   a malleable sheath having a first surface for engaging a tissue of the body, the malleable sheath comprising multiple layers, at least one of the electrical conductors being disposed between a first layer and a second layer of the malleable sheath for at least partially maintaining the position of the plurality of electrical conductors, the plurality of electrical connectors each extending radially from a common point.

27. The bone growth stimulator of claim 26, wherein at least one of the electrical conductors is disposed between third and fourth layers of the malleable sheath.

28. The bone growth stimulator of claim 27, wherein the malleable sheath comprises layers with none of the electrical conductors between them.

29. A bone growth stimulator for use with an orthopaedic device including an acetabular cup with a hemispherical exterior surface, the bone growth simulator comprising:
   a plurality of electrical conductors adapted to provide electrical stimulation to a bone; and
   a sheath comprising a hemispherical configuration and having a first surface for engaging the exterior surface and a second surface for engaging the bone, the sheath adapted for at least partially maintaining the position of the plurality of electrical conductors, the plurality of electrical connectors each extending radially from a common point.

30. The bone growth stimulator of claim 29, wherein plurality of electrical conductors are adapted for providing electrical stimulation at a plurality of voltages.

31. The bone growth stimulator of claim 29, wherein the plurality of electrical conductors are controllable by an external device.

32. The bone growth stimulator of claim 31, wherein the plurality of electrical conductors are adapted to receive power from the external device.

33. The bone growth stimulator of claim 29, wherein the orthopaedic device is one of a hip prosthesis, a knee prosthesis, an ankle prosthesis, a spinal prosthesis, a shoulder prosthesis, an elbow prosthesis, a wrist prosthesis, or a jaw prosthesis.

34. The bone growth stimulator of claim 29, wherein sheath comprises multiple layers, at least one of the electrical conductors being disposed between two layers of the sheath.

35. The bone growth stimulator of claim 29, wherein the sheath is provided without an insulation layer.

* * * * *